United States Patent
Takano et al.

(10) Patent No.: US 6,369,251 B1
(45) Date of Patent: Apr. 9, 2002

(54) METHOD FOR PURIFICATION OF POLYPRENYL COMPOUNDS

(75) Inventors: Michika Takano; Noriaka Gomi, both of Saitama (JP)

(73) Assignee: Nikken Chemicals Co., Ltd., Tokyo (JP)

(*) Notice: Subject to any disclaimer, the term of this patent is extended or adjusted under 35 U.S.C. 154(b) by 0 days.

(21) Appl. No.: 09/553,852

(22) Filed: Apr. 21, 2000

(30) Foreign Application Priority Data

Apr. 23, 1999 (JP) .......................................... 11-116483

(51) Int. Cl.⁷ ................................................ C11B 3/00
(52) U.S. Cl. ....................................... 554/208; 554/206
(58) Field of Search ........................... 554/175, 63, 65, 554/206, 208; 260/404

(56) References Cited

U.S. PATENT DOCUMENTS

| | | |
|---|---|---|
| 4,655,973 A | 4/1987 | Yamatsu et al. |
| 4,757,140 A | 7/1988 | Deluca et al. ................. 536/27 |
| 4,841,038 A | 6/1989 | Deluca et al. ............... 548/542 |
| 4,917,829 A | 4/1990 | Yamatsu et al. |

FOREIGN PATENT DOCUMENTS

| | | | | |
|---|---|---|---|---|
| GB | 781809 | 8/1957 | | |
| JP | 63-32058 | 6/1988 | | |
| JP | 63-34855 | 7/1988 | | |
| WO | WO 94/22818 | * 10/1994 | ......... | C07C/403/20 |
| WO | 94/22818 | 10/1994 | | |

OTHER PUBLICATIONS

344 New England Journal of Medicine 1561 (1996).
1966 Journal of Chemical Society 2154 (1966).
Patent Abstracts of Japan 56140949.
Patent Abstract of Japan 57106638.
K. Ashizawa et al., "The Crystal Structure of 3,7,11,15–tetramethyl–2,4,6,10,14–all trans–hexadecapentaenoic acid", 33 Chem. Pharm. Bull. 7, 3062–64 (1985).

* cited by examiner

*Primary Examiner*—Deborah D. Carr
(74) *Attorney, Agent, or Firm*—Greenblum & Bernstein, P.L.C.

(57) ABSTRACT

A method for purification of a polyprenyl compound, which comprises the step of recrystallizing a polyprenyl compound, preferably (2E, 4E, 6E, 10E)-3,7,11,15-tetramethyl-2,4,6,10,14-hexadecapentaenoic acid by using a solvent comprising an alcohol.

7 Claims, No Drawings

METHOD FOR PURIFICATION OF POLYPRENYL COMPOUNDS

BACKGROUND OF THE INVENTION

1. Field of the Invention

The present invention relates to a method for purification of a polyprenyl compound.

2. Related Art (2E, 4E, 6E, 10E)-3,7,11,15-Tetramethyl-2,4,6,10,14-hexadecapentaenoic acid, which is one of polyprenyl compounds, has been known to have suppressing effect on recurrence of hepatic carcinoma (New England Journal of Medicine, 334, 1516 (1996)).

Polyprenyl compounds are a known class of compounds as disclosed in Japanese Patent Publication (Kokoku) Nos. 63-32058, 63-34855 and the like. As described in the above patent publications, a purification method for polyprenyl compounds is known which comprises the step of subjecting crude crystals of polyprenyl compounds obtained by a reaction to crystallization and recrystallization in n-hexane.

SUMMARY OF THE INVENTION

The conventional purification of polyprenyl compounds using n-hexane fails to completely remove impurities produced during or after the reaction. The inventors of the present invention eagerly conducted researches on purification of polyprenyl compounds that are susceptible to oxidization with light, air and the like. As a result, they found that peroxides or oxides, which were not completely removable by the treatment using n-hexane, were perfectly removed by stirring a crude polyprenyl compound in an alcoholic solvent such as methanol for several hours with warming, and then carrying out recrystallization. They also found that a target polyprenyl compound of an extremely high purity was obtained by the above procedure. The present invention was achieved on the basis of these findings.

The present invention thus provides a method for purification of a polyprenyl compound, which comprises the step of recrystallizing a polyprenyl compound, preferably (2E, 4E, 6E, 10E)-3,7,11,15-tetramethyl-2,4,6,10,14-hexadecapentaenoic acid represented by Formula (I), by using a solvent comprising an alcohol.

(I)

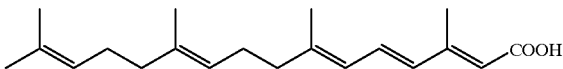

According to preferred embodiments of the present invention, there are provided:

the aforementioned method for purification of a polyprenyl compound, wherein the polyprenyl compound is a polyprenylcarboxylic acid;

the aforementioned method for purification of a polyprenyl compound, wherein the polyprenyl compound is (2E, 4E, 6E, 10E)-3,7,11,15-tetramethyl-2,4,6,10,14-hexadecapentaenoic acid;

the aforementioned method for purification of a polyprenyl compound, wherein the solvent is an alcohol, preferably methanol; and the aforementioned method for purification of a polyprenyl compound, wherein a purity of the polyprenyl compound after the purification step is 99.9% or higher.

PREFERRED EMBODIMENTS OF THE INVENTION

A particularly preferred example of the polyprenyl compound which can be purified by the method of the present invention includes (2E, 4E, 6E, 10E)-3,7,11,15-tetramethyl-2,4,6,10,14-hexadecapentaenoic acid whose chemical formula is shown above. Other examples of the polyprenyl compounds include conjugated polyprenylcarboxylic acids (polyprenoic acids) such as 3,7,11,15-tetramethyl-2,4,6,10,14-hexadecapentaenoic acid and esters thereof disclosed in Japanese Patent Publication (Kokoku) No. 63-34855, more specifically, such as (2E, 4E, 6E, 10E)-3,7,11,15-tetramethyl-2,4,6,10,14-hexadecapentaenoic acid ethyl ester, which can be used as a raw material for the preparation of (2E, 4E, 6E, 10E)-3,7,11,15-tetramethyl-2,4,6,10,14-hexadecapentaenoic acid.

The polyprenyl compounds used in the present invention can be synthesized by a known method disclosed in Japanese Patent Publication (Kokoku) No. 63-32058 and Journal of Chemical society (C), 2154, 1966.

The recrystallization using a solvent comprising an alcohol is performed by recrystallizing crude crystals of a polyprenyl compound, or by recrystallizing crystals of a polyprenyl compound of a relatively high purity. As the alcoholic solvent used for the recrystallization, examples include methanol, ethanol, 1-propanol, 2-propanol, 1-butanol, 2-butanol, 3-methylpropanol, 3-methyl-1-butanol and the like, and among them, methanol is preferably used. In addition, a solvent containing an alcohol such as methanol and ethanol can also be used for the present invention. Examples of a solvent which can be used as a mixture or a suspension with an alcohol include, for example, halogenated solvents such as carbon tetrachloride, chloroform and dichloromethane, hydrocarbonic solvents such as n-pentane, n-hexane, n-heptane, isooctane, cyclohexane, methylcyclohexane, toluene, benzene and xylene, ether solvents such as diethyl ether, diisopropyl ether, t-butyl methyl ether, methyltetrahydrofuran, tetrahydrofuran, 1,4-dioxane, 1,1-diethoxypropane, 1,1-dimethoxymethane and 2,2-dimethoxypropane, ester solvents such as ethyl acetate and ethyl formate, other organic solvents such as acetonitrile, N,N-dimethylacetamide, N,N-dimethylformamide, dimethyl sulfoxide, acetone, methyl ethyl ketone, methyl isopropyl ketone, petroleum ether, and water.

The recrystallization according to the present invention is performed by dissolving a polyprenyl compound in a solvent comprising an alcohol, preferably an alcoholic solvent such as methanol and ethanol, most preferably methanol, and then cooling the solution to allow precipitation of crystals.

Specifically, a solvent comprising an alcohol is added to a polyprenyl compound, and the mixture is stirred within a temperature ranging from room temperature to a boiling temperature of the solvent comprising an alcohol under heating. Then, the solution is left stand to allow precipitation of crystals.

More specifically, when methanol is used as the solvent comprising an alcohol, the solution is warmed to generally 50 to 70° C., preferably about 60° C. and stirred generally for about 1 hour or more, preferably about 3 hours. Then, the solution is left stand for cooling to allow precipitation of crystals.

By carrying out the purification of the present invention, a high purity of 99.9% or higher can be obtained for (2E, 4E, 6E, 10E)-3,7,11,15-tetramethyl-2,4,6,10,14-hexadecapentaenoic acid and the like. One of advantages of the high purity of the compound obtained by the present invention may include the following. Namely, for a government approval of the manufacture of a new drug, structural determination, and evaluation of toxicity and pharmacological action as well as normalization of a product are required for an impurity contained at a content ratio of 0.1% or more. Therefore, the process of obtaining a highly purified compound by the purification of the present invention is useful to obtain a drug with an excellent quality.

EXAMPLES

The present invention will be explained more specifically with reference to examples. However, the scope of the present invention is not limited to the following examples.

Reference Example 1

(2E, 4E, 6E, 10E)-3,7,11,15-tetramethyl-2,4,6,10, 14-hexadecapentaenoic acid ethyl ester Under argon atmosphere, sodium ethoxide (18.1 g) was suspended in N,N-dimethylformamide (200 ml), and the suspension was added dropwise with triethyl-3-methyl-4-phosphono-crotonate (purity: 80%, 58.4 g) dissolved in N,N-dimethyl-formamide (50 ml) at a low temperature. The reaction mixture was stirred at room temperature for 20 minutes, and then added dropwise with trans, trans-farnesal (37.1 g) dissolved in N,N-dimethylformamide (50 ml) on an ice bath. The mixture was stirred for 4 hours, then added with ice water and acetic acid, and extracted with n-hexane under a weakly acidic condition. After the extraction, the n-hexane layer was washed with 75% aqueous methanol and then with brine, and dried over magnesium sulfate. The solvent was evaporated under reduced pressured to obtain (2E, 4E, 6E, 10E)-3,7,11,15-tetramethyl-2,4,16,10,14-hexadecapentaenoic acid ethyl ester (48.6 g).

Reference Example 2

(2E, 4E, 6E, 10E)-3,7,11,15-tetramethyl-2,4,6,10, 14-hexadecapentaenoic acid

Under argon atmosphere, potassium hydroxide (19.4 g) was dissolved in 2-propanol (200 ml) under reflux, and the solution was added dropwise with (2E, 4E, 6E, 10E)-3,7, 11,15-tetramethyl-2,4,6,10,14-hexadecapentaenoic acid ethyl ester (48.6 g) dissolved in 2-propanol (50 ml). After the mixture was stirred for 10 minutes under reflux, ice water was added to the reaction mixture and the aqueous layer was washed with n-hexane. The aqueous layer was made acid with 10% aqueous hydrochloric acid, and then extracted with diisopropyl ether. The organic layer was washed with brine and dried over magnesium sulfate, and the solvent was evaporated under reduced pressure to obtain crude (2E, 4E, 6E, 10E)-3,7,11,15-tetramethyl-2,4,6,10,14-hexadecapentaenoic acid (35.7 g, purity: 62.2%) as orange crystals.

Example 1

Purification of (2E, 4E, 6E, 10E)-3,7,11,15-tetramethyl-2,4,6,10,14-hexadecapentaenoic acid Under argon atmosphere, methanol (35 ml) was added to the crude (2E, 4E, 6E, 10E)-3,7,11,15-tetramethyl-2,4,6,10, 14-hexadecapentaenoic acid (17.8 g) obtained in Reference Example 2, and the crystals were dissolved with warming. The solution was left stand overnight at an external temperature of −20° C. to allow precipitation of crystals. The deposited crystals were collected by filtration to obtain roughly purified (2E, 4E, 6E, 10E)-3,7,11,15-tetramethyl-2, 4,6,10,14-hexadecapentaenoic acid (6.9 g, purity: 94.5%) as yellow crystals. Subsequently, the roughly purified product was added with methanol (15 ml), and the solution was maintained at 60° C. for 3 hours with stirring under argon atmosphere. The mixture was left stand at room temperature, and the deposited crystals were collected by filtration to obtain (2E, 4E, 6E, 10E)-3,7,11,15-tetramethyl-2,4,6,10,14-hexadecapentaenoic acid (5.8 g) as light yellow, crystals.

$^1$H-NMR (CDCl$_3$): δ1.60 (s, 3H), 1.61 (s, 3H), 1.68 (s, 3H), 1.86 (s, 3H), 1.96–2.09 (m, 4H), 2.15 (s, 2H), 2.16 (s, 2H), 2.34 (s, 3H), 5.06–5.10 (m, 2H), 5.77 (s, 1H), 5.98 (d, 1H, J=11.2 Hz), 6.20 (d, 1H, J=15.1 Hz), 6.90 (dd, 1H, J=11.2, 15.1 Hz), 11.8 (br, 1H)

$^{13}$C-NMR (CDCl$_3$): δ14.2, 16.2, 17.4, 17.8, 25.8, 26.5, 26.8, 39.8, 40.4, 117.1, 123.3, 124.1, 124.8, 131.2, 131.8, 133.1, 135.5, 144.6, 155.4, 172.3

Melting point: 78° C.

Reference Example 3

Purification of (2E, 4E, 6E, 10E)-3,7,11,15-tetramethyl-2,4,6,10,14-hexadecapentaenoic acid by a conventional method The crude (2E, 4E, 6E, 10E)-3,7,11,15-tetramethyl-2,4,6, 10,14-hexadecapentaenoic acid (17.8 g) obtained in Reference Example 2 was dissolved in n-hexane (35 ml) with warming, and the solution was left stand overnight at an external temperature of −20° C. to allow the precipitation of crystals. The deposited crystals were collected by filtration to obtain roughly purified (2E, 4E, 6E, 10E)-3,7,11,15-tetramethyl-2,4,6,10,14-hexadecapentaenoic acid (6.3 g, purity: 94.4%) as yellow crystals. The roughly purified product was recrystallized from n-hexane (15 ml) to obtain (2E, 4E, 6E, 10E)-3,7,11,15-tetramethyl-2,4,6,10,14-hexadecapentaenoic acid (5.6 g, purity: 99.2%) as light yellow crystals.

Reference Example 4

Re-purification of (2E, 4E, 6E, 10E)-3,7,11,15-tetramethyl-2,4,6,10,14-hexadecapentaenoic acid by conventional method The (2E, 4E, 6E, 10E)-3,7,11,15-tetramethyl-2,4,6,10,14-hexadecapentaenoic acid (3 g, purity of 99.2%) purified in Reference Example 3 was dissolved in n-hexane (6 ml) with warming, and the solution was left stand at room temperature to allow the precipitation of crystals. The deposited crystals were collected by filtration to obtain (2E, 4E, 6E, 10E)-3,7,11,15-tetramethyl-2,4,6,10,14-hexadecapentaenoic acid (2.8 g, yield: 93%) as light yellow crystals.

Test Example 1

The results of purities and determined peroxide values of (2E, 4E, 6E, 10E)-3,7,11,15-tetramethyl-2,4,6,10,14-hexadecapentaenoic acid obtained in Example 1 and Reference Example 3 are shown in Table 1.

Purities were measured by high performance liquid chromatography.

The determination of the peroxide values was performed by the method described in the British Pharmacopeia. About 1 g of each sample was accurately weighed in a stoppered Erlenmeyer flask, and the sample was added with chloroform (15 mL) and dissolved. The solution was added with acetic acid (20 mL), and the mixture was shaken gently. Air in the flask was sufficiently substituted with argon atmosphere, and the mixture was added with 1 mL of saturated potassium iodide solution prepared just before use, and the mixture was left stand for 10 minutes in a dark place. Then, the mixture was added with 30 mL of water and shaken vigorously. The liberated iodine was titrated with 0.01 mL/L sodium thiosulfate solution (indicator: 2 mL of the starch test solution). The titration was terminated when the purplish red color of the solution disappeared. Correction was made by performing a blank test in the same manner.

The peroxide value was calculated by using the following equation.

Peroxide value (meq/kg)=10f(a−b)/Sampled weight (g)

a: Titration volume (mL) of 0.01 mol/L $Na_2S_2O_3$ solution
b: Titration volume (mL) of 0.01 mol/L $Na_2S_2O_3$ solution in the blank test
f: Factor of 0.01 mol/L $Na_2S_2O_3$ solution

TABLE 1

| Sample | Purity before crystallization (%) | Purity of roughly purified product (%) | Purity after recrystallization (%) | Peroxide value (meq/kg) |
|---|---|---|---|---|
| Reference Example 3 | 62.2 | 94.4 | 99.2 | 3.0 |
| Example 1 | | 94.5 | 99.9 | 0 |

From the results shown in Table 1, as well as from the amounts (yields) and the purities of the target compound obtained in Example 1 and Reference Example 3, it is apparent that the purification by using an alcohol such as methanol according to the present invention can give a purity of 99.9% or higher of the target compound and achieve complete removal of peroxides (give peroxide value of 0), while the purification can give almost the same recovery rate of the target compound as the purification by the conventional method.

Test Example 2

Purity of the (2E, 4E, 6E, 10E)-3,7,11,15-tetramethyl-2,4,6,10,14-hexadecapentaenoic acid obtained in Reference Example 4 was determined as 99.5% (the purity of 99.2% was improved up to 99.5%). From the result, it can be understood that purification by repetition of the conventional method merely results in gradual decrease of the recovery, and it is difficult to obtain a product of a high purity, i.e., 99.9% or higher.

The present disclosure relates to subject matter contained in priority Japanese Patent Application No. 116483/1999, filed on Apr. 23, 1999, the contents of which is herein expressly incorporated by reference in its entirety.

What is claimed is:

1. A method for purification of a polyprenyl compound, which comprises the step of recrystallizing the compound by using a solvent comprising an alcohol, wherein the compound is 3,7,11,15-tetramethyl-2,4,6,10,14-hexadecapentaenoic acid.

2. The method for purification of a polyprenyl compound according to claim 1, wherein the polyprenyl compound is (2E, 4E, 6E, 10E)-3,7,11,15-tetramethyl-2,4,6,10,14-hexadecapentaenoic acid.

3. The method for purification of a polyprenyl compound according to claim 1, wherein the solvent is an alcohol.

4. The method for purification of a polyprenyl compound according to claim 2, wherein the solvent is an alcohol.

5. The method for purification of a polyprenyl compound according to claim 3, wherein the alcohol is methanol.

6. The method for purification of a polyprenyl compound according to claim 1, wherein a purity of the polyprenyl compound after the purification step is 99.9% or higher.

7. The method for purification of a polyprenyl compound according to claim 5, wherein a purity of the polyprenyl compound after the purification step is 99.9% or higher.

* * * * *

UNITED STATES PATENT AND TRADEMARK OFFICE
CERTIFICATE OF CORRECTION

PATENT NO. : 6,369,251 B1
DATED : April 9, 2002
INVENTOR(S) : M. Takano et al.

It is certified that error appears in the above-identified patent and that said Letters Patent is hereby corrected as shown below:

<u>Title page,</u>
Item [75], Inventors, "Noriaka" should be -- Noriaki --.

Signed and Sealed this

Fourteenth Day of January, 2003

JAMES E. ROGAN
*Director of the United States Patent and Trademark Office*